(12) United States Patent
Wewer et al.

(10) Patent No.: US 9,757,216 B2
(45) Date of Patent: Sep. 12, 2017

(54) OPTICAL MEASURING SYSTEM AND METHOD FOR OPTICALLY MEASURING AN OBJECT IN A THREE-DIMENSIONAL MANNER

(71) Applicant: SIRONA DENTAL SYSTEMS GMBH, Bensheim (DE)

(72) Inventors: Lukas Wewer, Duisburg (DE); Mark Weber, Moers (DE); Georg Wiora, Cologne (DE)

(73) Assignee: Dentsply International Inc., York, PA (US)

( * ) Notice: Subject to any disclaimer, the term of this patent is extended or adjusted under 35 U.S.C. 154(b) by 0 days.

(21) Appl. No.: 15/038,642

(22) PCT Filed: Nov. 24, 2014

(86) PCT No.: PCT/EP2014/075363
§ 371 (c)(1),
(2) Date: May 23, 2016

(87) PCT Pub. No.: WO2015/075215
PCT Pub. Date: May 28, 2015

(65) Prior Publication Data
US 2016/0296304 A1    Oct. 13, 2016

(30) Foreign Application Priority Data
Nov. 22, 2013   (DE) .................. 10 2013 223 894

(51) Int. Cl.
*G01C 11/12*    (2006.01)
*A61C 9/00*    (2006.01)
(Continued)

(52) U.S. Cl.
CPC .............. *A61C 9/006* (2013.01); *A61B 1/24* (2013.01); *G01B 11/25* (2013.01); *G02B 1/11* (2013.01);
(Continued)

(58) Field of Classification Search
CPC .... G01B 11/24; G01B 11/25; G01B 2210/50; G01B 2290/45; G01B 9/02044;
(Continued)

(56) References Cited

U.S. PATENT DOCUMENTS 6,252,717 B1 *   6/2001   Grosskopf .............. G01B 9/04
                                                                250/234
6,697,164 B1 *   2/2004   Babayoff ................ A61B 1/24
                                                                356/601

(Continued)

*Primary Examiner* — Michael P Stafira
(74) *Attorney, Agent, or Firm* — David A. Zdurne; Douglas J. Hurq; Leana Levin (57) ABSTRACT

The invention relates to an optical measuring system (1) and to a method for measuring an object (9) in a three-dimensional manner. The measuring system (1) has at least one lens array (5), a first convex lens (6) arranged downstream, a second convex lens (8) which is arranged further downstream and which faces an object (9) to be measured, and additionally a means (7) which absorbs incident light or deflects incident light out of the illuminating beam path and which is arranged upstream of the second convex lens (8) or on the second convex lens (8) on a second convex lens (8) face facing the first convex lens (6) in the region of the optical axis (10).

15 Claims, 3 Drawing Sheets

(51) Int. Cl.
| | |
|---|---|
| *G01B 11/25* | (2006.01) |
| *G02B 21/00* | (2006.01) |
| *A61B 1/24* | (2006.01) |
| *G02B 1/11* | (2015.01) |
| *G02B 3/00* | (2006.01) |
| *G02B 5/00* | (2006.01) |
| *G02B 5/09* | (2006.01) |
| *H04N 13/02* | (2006.01) |

(52) U.S. Cl.
CPC .......... *G02B 3/0006* (2013.01); *G02B 5/003* (2013.01); *G02B 5/09* (2013.01); *G02B 21/004* (2013.01); *G02B 21/008* (2013.01); *G02B 21/0032* (2013.01); *H04N 13/0203* (2013.01)

(58) Field of Classification Search
CPC .............. G01B 9/02079; G01B 9/0209; G01B 9/02091; G01B 9/02007; G01B 9/02008; G01B 9/0201; G01B 9/02032; G01B 9/02045; G01B 11/2513
See application file for complete search history.

(56) References Cited

U.S. PATENT DOCUMENTS

| | | | |
|---|---|---|---|
| 2005/0283065 A1* | 12/2005 | Babayoff | A61B 1/00009 600/407 |
| 2010/0099984 A1* | 4/2010 | Graser | G01B 11/24 600/425 |

\* cited by examiner

OPTICAL MEASURING SYSTEM AND METHOD FOR OPTICALLY MEASURING AN OBJECT IN A THREE-DIMENSIONAL MANNER

TECHNICAL FIELD

The invention relates to an optical measuring system and a method for measuring an object in a three-dimensional manner, the measuring system having at least one lens array, a first convex lens arranged downstream of the lens array in the direction of an illuminating beam path as well as a second convex lens arranged downstream of the first convex lens in the direction of the illuminating beam path and facing an object to be measured.

BACKGROUND OF THE INVENTION

Optical measuring systems for measuring objects in a three-dimensional manner that use a lens array, for example a grid of microlenses having round lenses, are known from the prior art.

WO 00/08415 A1 describes, for example, a measuring system for measuring objects in a three-dimensional manner via a matrix of light points projected onto the object. The design of the measuring system is confocal and the matrix of light points is, for example, generated via a microlens array.

A similar optical measuring system having a confocal design for three-dimensional measuring is known from EP 0 485 803 A1, in which a lighting grid is described that is generated via a lens array.

Lens arrays frequently comprise round lenses arranged, for example, in a square or hexagon pattern and therefore have spaces between the individual lenses. These spaces are often made of the same material as the lenses and therefore are often also transparent such that light can also penetrate them. For example, with a flat surface of spaces and orthogonal impingement, this light passes unbroken through the spaces, while light that impinges orthogonally onto the lenses of the lens array is diffracted or focused towards their respective focal point by said lenses. Therefore, the light that impinges on the spaces does not follow the desired light path through the lenses of the lens array. However, if this light remains in the light path or measuring system, it can adversely affect the imaging quality of the measuring system.

To prevent the illumination of the spaces and thus the occurrence of interfering light, the spaces can, for example, be coated with an opaque coating. This can prevent light from being transmitted through the spaces.

If the spaces are coated with an absorbent surface, it is possible to largely or even almost completely absorb the impinging light.

However, the spaces can also be coated with a coating that reflects light off to the side or filled with an appropriate medium. For example, a coating of microstructures, such as reflective cones or pyramids, can be provided, through which the impinging light is blocked out or directed out of the light path.

Known examples of coatings for spaces in lens arrays include chromium or chromium oxide coatings.

However, one disadvantage of the coating of the spaces is the additionally necessary process step of coating that leads to additional costs for the production of the lens array.

Depending on the coating, it can also be that the impinging light is not fully absorbed on the coating or reflected in the desired direction but is at least partially reflected diffusely or scattered. As a result, this light remains in the system and as scattered light adversely affects the imaging quality of the measuring system. Scattered light refers to light that does not follow the desired light path but propagates diffusely through the measuring system.

Furthermore, there is also the possibility of avoiding the spaces entirely by designing the lens array with square lenses. However, manufacturing such lens arrays is more laborious and therefore more expensive.

An optical configuration is known from US 2007/0296956 A1 that makes it possible to remove beams that are not diffracted by an object to be measured and would falsify the measurement result from a measurement beam path via an absorbent means.

It is therefore the object of the invention to provide an optical measuring system having a lens array that does not have any of the aforementioned problems and disadvantages.

SUMMARY OF THE INVENTION

The invention relates to an optical measuring system for measuring an object in a three-dimensional manner that has at least one light source that emits illuminating beams, a lens array comprising a plurality of lenses, a first convex lens arranged downstream of the lens array in the direction of propagation of the illuminating beams along an illuminating beam path as well as a second convex lens arranged downstream of the first convex lens in the direction of propagation of the illuminating beam path and facing an object to be measured. Furthermore, the optical measuring system comprises a means that absorbs impinging light or directs it out of the illuminating beam path. This means is arranged in the direction of propagation of the illuminating beams upstream of the second convex lens or on the second convex lens on a side of the second convex lens facing the first convex lens. Furthermore, in a plane that is essentially orthogonal to an optical axis of the measuring system, the means extends over an area that includes the optical axis of the measuring system or is spaced from said optical axis by no more than ⅙ of the diameter of the first context lens.

A lens array comprises a plurality of lenses that are as identical as possible and arranged next to each other in a single plane such that their focal planes coincide. The focal plane of a lens refers to a plane in which the focal point of the lens lies, that runs parallel to the lens or orthogonal to the optical axis of the lens and in which light that impinges parallel on the lens is therefore focused onto a focal point. The individual lenses of the lens array divide, for example, illuminating beams that impinge orthogonally into a plurality of individual beams that each produce a focal point in a common focal plane of all lenses of the array such that a matrix of light points is produced in this common focal plane in particular.

For reasons relating to manufacturing in particular, lens arrays frequently have spaces between the lenses that usually also comprise the same material as the lenses without further coating and are therefore translucent. In contrast to the lenses, the spaces usually take the form of flat surfaces. This makes it possible for a portion of the illuminating beams that impinge orthogonally onto the lens array to travel through the spaces without deflection. This portion of the illuminating beams therefore does not follow the rest of the provided light path of the measuring system but instead runs diffusely through the rest of the measuring system and interferes with the image quality. According to the invention, this light can be removed from the measuring system by way of the means at about the height of the second convex lens in the area of the optical axis, as a result of which the image quality of the measuring system increases.

The first convex lens can, for example, be located at the location of the intermediate image of the optical measuring system. However, for reasons related to technical implementation, the position of the first convex lens can also differ from the location of the intermediate image. Such a lens is often referred to as a field lens.

The second convex lens, which faces the object, is frequently referred to as an objective lens.

The optical axis of a system made up of optical components, such as the optical measuring system according to the invention, results from the axes of symmetry of the optical elements. For example, most of the focal points in a confocal measuring system are on the optical axis.

The part of the light of the illuminating beams that impinges on the means is absorbed or directed out of the measuring system by the means. Because the means removes the light from the measuring system, it can also be referred to as a light trap or anti-pinhole. In particular, it is possible to remove interfering light from the measuring system using the means.

For example, if parallel illuminating beams impinge orthogonally onto the lens array and are transmitted in the area of the spaces without deflection, the light that passes through the spaces impinges orthogonally onto the first convex lens. If the means according to the invention for removing this light is located in the area of the focal plane of the first convex lens, a relatively small extension of the means in terms of area in the plane orthogonal to the optical axis of the system suffices if the means is arranged in the area of the optical axis because the light that entered through the spaces collects in the focal point of the first convex lens, i.e., at the intersection of the optical axis of the system and the focal plane of the first convex lens.

The means can, for example, have absorbent surfaces. As a result of this, for example, an absorption of 96%, or with special coatings even an absorption of up to 99.5% of the light that impinges on this surface, can be achieved.

The means can also have reflective surfaces that direct the impinging light out of the rest of the light path. The light that impinges on the means can, for example, be redirected onto an absorbent light trap arranged outside of the light path via reflective surfaces, i.e., onto a means that removes light from the system via absorption.

For a lens array having translucent spaces, the proportion of the light that enters through the lens array without deflection and, at least potentially, interferes with the imaging quality is calculated from the fill factor of the lenses of the lens array used. In a square arrangement of round lenses, the theoretically achievable fill factor of the lenses is 78.5%. Accordingly, the spaces make up 21.5% of the area. However, the technical implementation of a microlens array frequently requires, for example, additional spaces, which is why the proportion of spaces of a microlens array typically increases to more than 35%. This light can be removed from the light path of the system via the means according to the invention.

However, it is possible for light that is scattered back from the object, contains image information and travels through the measuring system in the opposite direction of the illuminating beam path to be absorbed in the area of the means depending on the design of the means. Because the reflected scattering lobe, that is, the radiation characteristics, of strongly scattering reflective surfaces, for example a tooth, has a large opening angle, the relative proportion of the light coming from the object and being absorbed by the means is, however, relatively small. The decrease in intensity that takes place due to the provision of the means is negligible. As a result, the means according to the invention is particularly suitable for optical measuring systems in the dental field, e.g., dental cameras.

However, depending on the design of the means, the light scattered back from the object could also be reflected or scattered in the area of the means and remain in the measuring system as scattered light as a result. Because the light intensity scattered back from the object, such as a tooth, is, however, usually low overall, no significant proportion of scattered light is to be expected as a result of this. Reductions of the imaging quality resulting from this can thus also be disregarded.

The means can advantageously be formed as part of the second convex lens.

This can be a variant of the means that is particularly easy to manufacture and/or adjust in the measuring system. For example, the means can be designed as a light-absorbing, matte-black surface, e.g., a corresponding coating, which is applied near the center of the surface of the second convex lens that faces the first convex lens. The means could also partially extend into the second convex lens.

The optical measuring system can advantageously be a confocal measuring system.

Confocal measuring systems typically have a shutter or a pinhole in an image plane or intermediate image plane. The yield of light when it passes through this shutter can be improved by using a lens array, the previously described disadvantages of which can in turn be avoided or at least reduced by the means according to the invention.

The plurality of lenses of the lens array can advantageously be round, it being possible for the lens array to have at least one space between the plurality of round lenses.

In particular, lens arrays having very small lenses and spacing between the lenses, for example, grids of microlenses, often cannot be manufactured with square lenses that fill the entire surface due to reasons related to production. Lens arrays having an arrangement of lenses with a round outer contour in a square or hexagonal package are frequently easy to implement from a technical perspective. However, such lens arrays have spaces between the round lenses, the spaces usually being made of the same material as the lenses and therefore translucent due to reasons related to production.

Such lens arrays are, for example, produced from a carrier manufactured in a masking process, such as the masking processes customary in semiconductor technology, and from a subsequently fused surface. For production reasons, the proportion of the spaces of such lens arrays is usually approx. 35%.

The at least one space can advantageously be translucent and have a plane-parallel surface.

From a manufacturing point of view, it is particularly easy to make the spaces from the same material as the lenses. When the spaces are designed flat, light that impinges orthogonally onto the spaces can penetrate through all spaces without changing its direction of propagation such that it is projected by the first convex lens onto a single focal point in the area of the optical axis at the height of the focal plane of the first convex lens where it can be removed from the light path of the measuring system via the means according to the invention.

Because all of the light that travels through the spaces and does not contribute to the measurement of the object is collected in a single focal point where it is removed from the system by the means, it is possible on the one hand to make the means so large that the possibly all of the light that travels through the spaces is captured by the means. On the other hand, the size of the means can be so small that the smallest possible amount of light that travels through the lenses of the lens array is captured by the means.

The lens array can advantageously be arranged in such a way that the optical axis of the measuring system runs through a second space of the lens array.

As a result of this, all central beams of the light beams produced by the individual lenses of the lens array are at a distance from the optical axis such that these light beams, if possible, do not impinge on the means arranged around the optical axis or near the optical axis. This makes it possible to exclusively remove light that travels through the spaces of the lens array from the measuring system, whereas the light that is focused by the lenses of the lens array can be used to illuminate and measure the object without restriction.

The lens array can advantageously be arranged in such a way that the optical axis of the measuring system coincides with the center of one lens of the lens array.

Thanks to this alternative arrangement of the lens array relative to the optical axis of the measuring system, the position of the lens array in the measuring system is very well defined. This makes adjustment easier, for example.

The second convex lens can advantageously be arranged in the focal plane of the first convex lens.

Because of this, light that impinges orthogonally onto the first convex lens is focused onto the second convex lens, the focal point ideally being located at the intersection of the longitudinal axis or the lens surface of the second convex lens and the optical axis. Light from parallel illuminating beams that impinges orthogonally onto the lens and that travels through the spaces of the lens array is thus collected in a single focal point in the area of the second convex lens. Because of this, the means can be arranged directly on the second convex lens or be designed as part of the second convex lens, the size of the means in the plane orthogonal to the optical axis essentially only needing to correspond to the size of this focal point.

The means can advantageously be arranged in the focal plane of the first convex lens.

Because the illuminating beams typically form a parallel light beam that impinges orthogonally onto the lens array such that the light passing through the spaces typically also impinges orthogonally onto the first convex lens, this light collects in a single point in the focal plane of the first convex lens. If the means according to the invention is arranged in this focal plane, very small dimensions within this plane are already sufficient for capturing via the means all of the light that travels through the spaces of the lens array.

The means can advantageously be a light-absorbing matte-black surface.

This is a particularly simple option for removing the impinging light from the measuring system by means of absorption.

The means can advantageously be an n-sided, pyramidal mirror mirrored on the outer surfaces.

This allows the impinging light to be deflected out of the light path by means of reflection.

The means can advantageously be a conical mirror mirrored on the outside of the conical surface.

This is another option for directing the impinging light out of the light path.

The means can advantageously be a flat mirror inclined relative to the optical axis.

A flat mirror arranged in such a way allows the impinging light to be directed out of the light path in a particularly simple manner by means of reflection in a similar direction. The flat, reflective surface of the mirror can, for example, be arranged at an angle relative to the optical axis, which is less than 90°, for example 45°.

The lens array can advantageously be coated with an anti-reflective coating on both sides.

This reduces the proportion of light that is reflected on the surface of the lens array and thus prevents the formation of interfering scattered light.

The measuring system can advantageously be part of an intraoral dental camera.

Due to their area of application, intraoral dental cameras must not be too large or too heavy. It is therefore common to use microlens arrays as a lens array for the optical measurement configuration in the camera. Because such microlens arrays usually have translucent spaces between the lenses for reasons relating to manufacturing and because the means according to the invention is also very well suited for small structures, it is particularly suitable for use in intraoral dental cameras.

The intraoral dental camera can advantageously have a handle, a front part that can be inserted into an oral cavity and a beam deflector arranged on a free end of the front part.

This is a common embodiment of an intraoral dental camera that is designed for the production of images of teeth in the mouth of a patient. However, an intraoral camera according to the invention could, for example, also do without a beam deflector, for example, if the sensor is sufficiently small or only images of the incisors are to be taken.

Furthermore, the invention relates to a method for optically measuring an object in a three-dimensional manner via an optical measuring system, for example, the one described above. According to the method, illuminating beams reach the object at least through a lens array and at least a first and a second convex lens in the mentioned order downstream of the lens array in a direction of propagation of the illuminating beams along an illuminating beam path. A portion of the illuminating beams is absorbed upstream of or on the second convex lens in the area of an optical axis of the optical measuring system, in an area in the direction of propagation of the illuminating beams or directed out of the illuminating beam path.

Particularly when using lens arrays having translucent spaces, the method according to the invention makes it possible to easily remove interfering light, e.g., the light that travels through the spaces, from the light path used for measurement.

BRIEF DESCRIPTION OF THE DRAWINGS

The drawings depict exemplary embodiments of the invention. In the drawings.

DETAILED DESCRIPTION OF THE INVENTION

Figure 1:
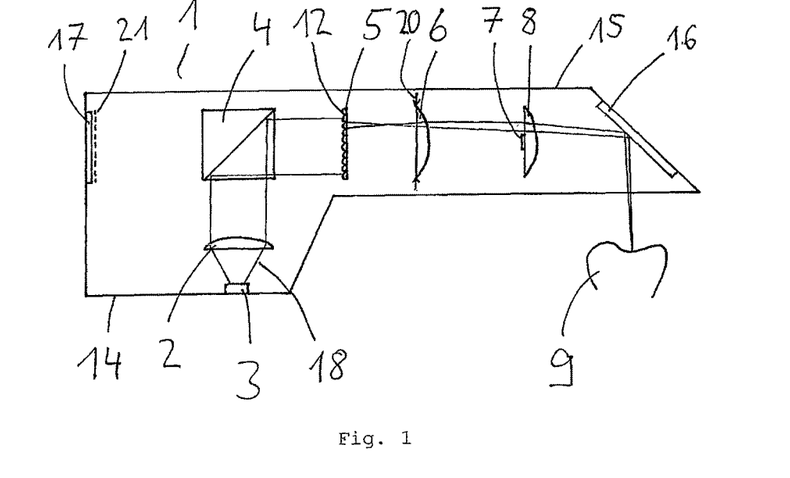
FIG. 1 shows a measuring system having an optical confocal measurement configuration and designed as an intraoral dental camera.

FIG. 1 shows a optical measuring system 1 designed as an intraoral dental camera, having a handle 14 and a front part 15 that can be inserted into the oral cavity of a patient. The central part of the optical components of the optical measuring system 1 is shown again in FIG. 2. For better clarity, only parts of light paths are drawn in the measuring devices shown. The central components or at least parts of said components could also be used in a measuring system 1 configured differently from the one in FIG. 1 to obtain a measuring system 1 according to the invention.

Figure 2:
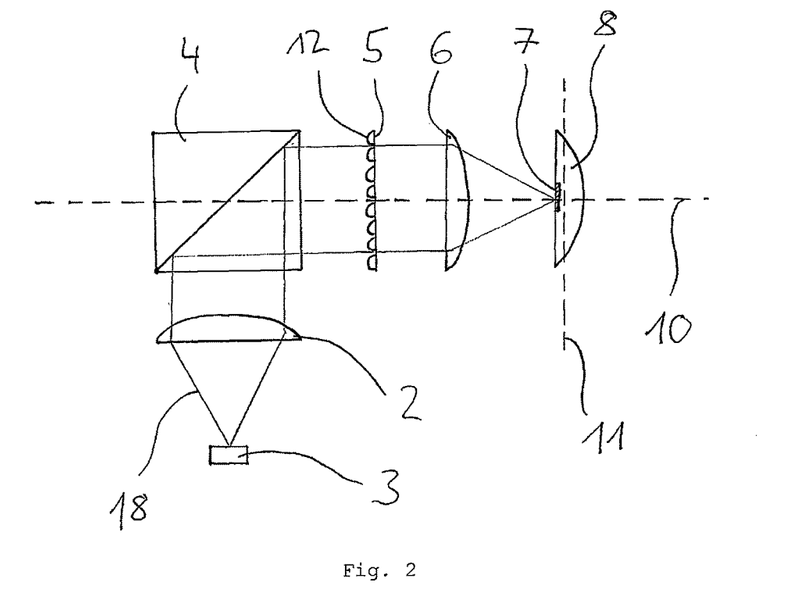
FIG. 2 shows a part of the optical confocal measurement configuration of the intraoral dental camera depicted in FIG. 1.

The light from illuminating beams 18 originating from a light source 3 is projected orthogonally onto a lens array 5 by a collector lens 2 via a beam splitter 4 as a parallel light beam.

The light of the light source 3 could also be directed to the camera via a light guide, for example, a glass fiber. Furthermore, it would also be possible to guide the light to the lens array 5 without deflecting it via the beam splitter 4. All previously known solutions for confocal measurement configurations, in particular those suitable for intraoral cameras, can be used.

Figure 4:
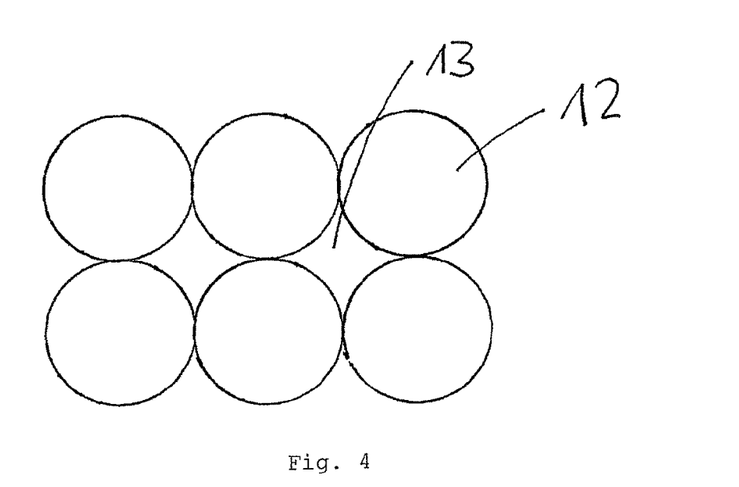
FIG. 4 shows a section of a lens array.

The lens array 5 comprises a plurality of lenses 12 that, for example, have a round outer contour and can be arranged in a parallel package such that there are spaces 13 between the lenses 12. Such a lens array 5 is shown in FIG. 4. The light of the illuminating beams 18 that impinges on the lenses 12 of the lens array 5 is divided into several essentially parallel light beams.

The lenses 12 could also be hexagonally arranged or have an elliptical shape. The arrangement, as well as the number of lenses 12 and their size, is essentially dependent on the type of application, for example, on the size of the object to be measured and/or the desired size of the optical measuring system 1.

The lenses 12 of the lens array 5 each produce a scaled-down image of the light source 3. The focal points of the individual lenses 12 of the lens array 5 are projected onto an object 9 via a first convex lens 6 and a second convex lens 8, which follow the lens array 5 in this order in the direction of propagation of the illuminating beams 18, as well as optionally via other optical components such that a field of light points forms on the object 9. A further optical component can, for example, be a beam deflector 16, as shown in FIG. 1.

Light scattered or reflected back from the object 9 passes through at least the second and the first convex lens 8, 6 as well as the lens array 5 in the opposite direction of the direction of propagation of the illuminating beams 18 and is, for example, projected onto a recording unit 17 via a shutter array or a shutter plate 21, as sketched in FIG. 1.

If the measuring system 1 according to the invention is, for example, used as an intraoral dental camera, as shown in the exemplary embodiment in FIG. 1, it is particularly important that the lens array 5 be as small as possible, e.g., a microlens array or microlens grid, because the overall configuration should have the smallest dimensions possible so that it can easily be held with one hand and at least partially inserted into a patient's mouth. The number of lenses 12 is essentially dependent on the desired number of light or measuring points or the desired resolution.

In the exemplary embodiment, the spaces 13 of the lens array 5 have essentially plane-parallel surfaces. As a result of this, light from the illuminating beams 18 that impinges orthogonally passes through the spaces 13 without changing direction, essentially unbroken and without deflection, whereas the light impinging onto the lenses 12 of the lens array 5 is diffracted by the refractive power of the lenses 12. While the light impinging onto the lenses 12 is subsequently diverted to the object 9 via the other components of the measuring system 1, in particular the first and second convex lens 6, 8, and the portion of the light scattered or reflected back from the object 9 essentially passes through the measuring system 1 in the opposite direction of the illuminating beams 18 and is projected onto the recording unit 17, the light that travels through the spaces 13 is located in the system as interfering light and adversely affects the imaging quality of the measuring system 1.

To remove this interfering light from the measuring system 1, the second convex lens 8 has a light-absorbing surface as a means 7 in the area surrounding an optical axis 10 of the measuring system 1. This can be, for example, a matte-black surface. Light that impinges onto the means 7 is absorbed at least for the most part.

Light that impinges orthogonally onto the lens array 5, said light being transmitted unbroken through the spaces 13, impinges orthogonally onto the first convex lens 6, which focuses said light. If the second convex lens 8, as shown in FIG. 2, is arranged in the area of a focal plane 11 of the first convex lens 6, the light that travels unbroken through the lens array 5 is focused onto the second convex lens 8 in the area of the optical axis 10, absorbed by the light-absorbing surface arranged in this area as a means 7 and thus removed from the light path used for the measurement of the object 9.

Another way to remove the light that travels through the spaces 13 from the light path is to direct the light from the measuring system 1 or at least from the light path of the illuminating beams 18, for example, via a reflective surface.

Figure 5:
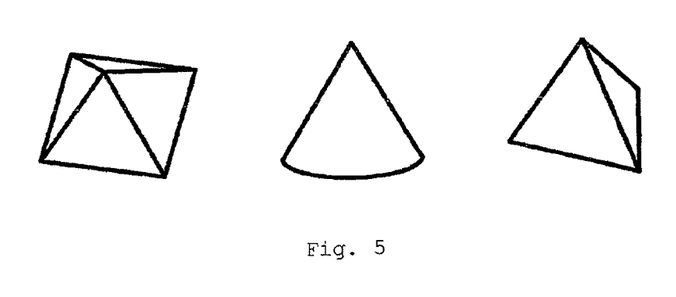
FIG. 5 shows two pyramidal and one conical mirror.

For this purpose, the means 7 can, for example, be designed as a mirror with a four-, three- or even n-sided pyramidal or conical mirrored outer surface with a tip pointing towards the first convex lens 6 and a base surface that can be arranged upstream of the second convex lens 8 or on the surface of the second convex lens 8. Corresponding mirror shapes for the means 7 are shown in FIG. 5.

Figure 6:
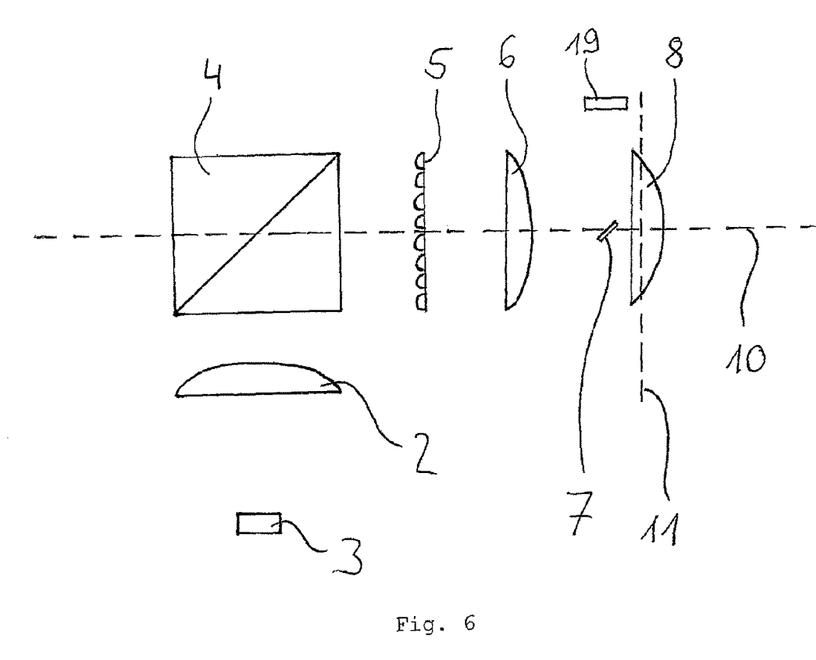
FIG. 6 shows a part of the optical confocal measuring system having a flat mirror as a means according to the invention.

The means 7 according to the invention can also be designed as a flat mirror that is arranged tilted with respect to the optical axis 10 of the measuring system 1 in the area of the optical axis 10 at a distance upstream of or on the second convex lens 8, as a result of which impinging light is directed out of the light path. This variant is shown in FIG. 6.

The light directed out of the light path can then be removed elsewhere outside of the light path via an absorber 19, i.e., an absorbent means. This has the advantage that one is not as restricted in terms of the size or the dimensions of the absorber 19 as one is for the absorption of the light within—or at least in the area of—the light path of the measuring system 1.

However, the light directed out of the light path could also, for example, be directed out of the entire measuring system 1 via other optical components.

If the lens array 5, as shown in FIG. 2, is oriented in such a way with respect to the optical axis 10 of the measuring system 1 that the optical axis 10 of the measuring system 1 passes through a space 13 of the lens array 5, it is possible to remove only light that travels through the spaces 13 of the lens array 5 from the light path using the means 7 while the light that travels through the lenses 12 of the lens array 5 is projected past the means 7 onto the object 9. For this purpose, however, the means 7 must be small enough with respect to a plane orthogonal to the optical axis 10 for the light paths of all beams produced by the lenses 12 of the lens array 5 to pass by the means 7. In this case, all of the beams produced by the lenses 12 of the lens array 5 and all of the focal points can be used to measure the object 9.

Figure 3:
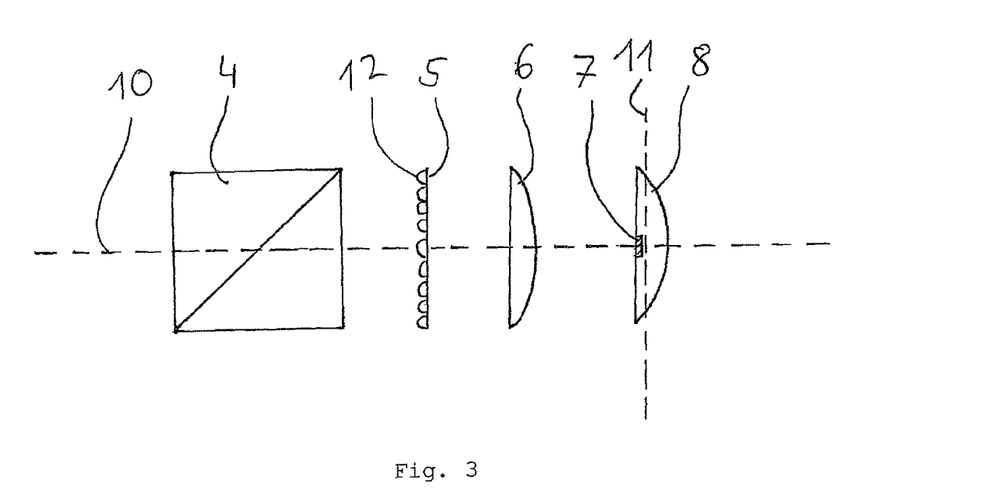
FIG. 3 shows another arrangement of a lens array in an optical confocal measuring system.

If the lens array 5 is arranged in such a way that the optical axis 10 passes through one of the lenses 12 of the lens array 5, as shown in FIG. 3, the lens array 5 can be adjusted particularly simply and reliably.

For this purpose, however, a portion of the light that travels through the lenses 12 is removed from the light path by the means 7 in addition to the light that travels through the spaces 13 of the lens array 5, and the lens 12 of the lens array 5, through which the optical axis 10 of the measuring system 1 passes, does not produce any light point, or produces at least a very restricted light point in terms of light intensity, on the object 9.

If the measuring system 1 according to the invention is, for example, implemented with optical components that are slightly tilted with respect to the optical axis 10 to, for example, remove back reflections of the optical components from the light path of the measuring system 1 used for projection, it can also be advantageous to arrange the means 7 at a slight distance from the optical axis 10. The means 7 could, for example, be arranged at a distance of up to $\frac{1}{6}$ of the diameter (20) of the first convex lens.

This could also be advantageous if the means 7 is arranged in the direction of propagation in front of the focal plane 11 of the first convex lens 6. It is, for example, also possible to consider that the means 7 spans an area in a plane orthogonal to the optical axis 10, said area being at a distance from the optical axis 10 and surrounding it.

LIST OF REFERENCE SYMBOLS

1 Optical measuring system
2 Collector lens
3 Light source
4 Beam splitter
5 Lens array
6 First convex lens
7 Means
8 Second convex lens
9 Object
10 Optical axis
11 Focal plane of the first convex, lens
12 Lens
13 Space
14 Handle
15 Front part insertable into the oral cavity
16 Beam deflector
17 Recording unit
18 Illuminating beams
19 Absorber
20 Diameter of the first convex lens
21 Shutter plate

The invention claimed is:

1. An optical measuring system for measuring an object in a three-dimensional manner, having
   at least one light source that emits illuminating beams,
   at least one lens array comprising a plurality of lenses, a first convex lens arranged downstream of the lens array in the direction of propagation of the illuminating beams along an illuminating beam path as well as a second convex lens arranged downstream of the first convex lens in the direction of propagation of the illuminating beams and facing an object to be measured,
   means for absorbing impinging light or directing said light out of the illuminating beam path, is arranged in the direction of propagation of the illuminating beams upstream of the second convex lens or on a side of the second convex lens facing the first convex lens on the second convex lens and extends over an area in a plane that is essentially orthogonal to an optical axis of the measuring system, said area including the optical axis of the measuring system or being spaced from said optical axis by no more than $\frac{1}{6}$ of the diameter of the first convex lens,
   wherein the plurality of lenses of the lens array are round and that the lens array has at least one space between the plurality of round lenses, and
   wherein the lens array is arranged in the optical measuring system in such a way that the optical axis of the measuring system passes through one of the spaces of the lens array.

2. The optical measuring system according to claim 1, wherein the means is designed as part of the second convex lens.

3. The optical measuring system according to claim 1, wherein the optical measuring system is a confocal measuring system.

4. An optical measuring system for measuring an object in a three-dimensional manner, having
   at least one light source that emits illuminating beams,
   at least one lens array comprising a plurality of lenses, a first convex lens arranged downstream of the lens array in the direction of propagation of the illuminating beams along an illuminating beam path as well as a second convex lens arranged downstream of the first convex lens in the direction of propagation of the illuminating beams and facing an object to be measured,
   means for absorbing impinging light or directing said light out of the illuminating beam path, is arranged in the direction of propagation of the illuminating beams upstream of the second convex lens or on a side of the second convex lens facing the first convex lens on the second convex lens and extends over an area in a plane that is essentially orthogonal to an optical axis of the measuring system, said area including the optical axis of the measuring system or being spaced from said optical axis by no more than $\frac{1}{6}$ of the diameter of the first convex lens,
   wherein the plurality of lenses of the lens array are round and that the lens array has at least one space between the plurality of round lenses, and
   wherein the at least one space is translucent and has plane-parallel surfaces.

5. The optical measuring system according to claim 1, wherein the lens array is arranged in the optical measuring system in such a way that the optical axis of the measuring system coincides with the center of a lens of the lens array.

6. The optical measuring system according to claim 1, wherein the second convex lens is arranged in the focal plane of the first convex lens.

7. The optical measuring system according to claim 1, wherein the means is arranged in the focal plane of the first convex lens.

8. The optical measuring system according to claim 1, wherein the means is a light-absorbing, matte-black surface.

9. An optical measuring system for measuring an object in a three-dimensional manner, having
- at least one light source that emits illuminating beams,
- at least one lens array comprising a plurality of lenses, a first convex lens arranged downstream of the lens array in the direction of propagation of the illuminating beams along an illuminating beam path as well as a second convex lens arranged downstream of the first convex lens in the direction of propagation of the illuminating beams and facing an object to be measured,
- means for absorbing impinging light or directing said light out of the illuminating beam path, is arranged in the direction of propagation of the illuminating beams upstream of the second convex lens or on a side of the second convex lens facing the first convex lens on the second convex lens and extends over an area in a plane that is essentially orthogonal to an optical axis of the measuring system, said area including the optical axis of the measuring system or being spaced from said optical axis by no more than ⅙ of the diameter of the first convex lens,
- wherein the means is an n-sided, pyramidal mirror mirrored on the outer surfaces.

10. An optical measuring system for measuring an object in a three-dimensional manner, having
- at least one light source that emits illuminating beams,
- at least one lens array comprising a plurality of lenses, a first convex lens arranged downstream of the lens array in the direction of propagation of the illuminating beams along an illuminating beam path as well as a second convex lens arranged downstream of the first convex lens in the direction of propagation of the illuminating beams and facing an object to be measured,
- means for absorbing impinging light or directing said light out of the illuminating beam path, is arranged in the direction of propagation of the illuminating beams upstream of the second convex lens or on a side of the second convex lens facing the first convex lens on the second convex lens and extends over an area in a plane that is essentially orthogonal to an optical axis of the measuring system, said area including the optical axis of the measuring system or being spaced from said optical axis by no more than ⅙ of the diameter of the first convex lens,
- wherein the means is a conical mirror mirrored on the outside of the conical surface.

11. An optical measuring system for measuring an object in a three-dimensional manner, having
- at least one light source that emits illuminating beams,
- at least one lens array comprising a plurality of lenses, a first convex lens arranged downstream of the lens array in the direction of propagation of the illuminating beams along an illuminating beam path as well as a second convex lens arranged downstream of the first convex lens in the direction of propagation of the illuminating beams and facing an object to be measured,
- means for absorbing impinging light or directing said light out of the illuminating beam path, is arranged in the direction of propagation of the illuminating beams upstream of the second convex lens or on a side of the second convex lens facing the first convex lens on the second convex lens and extends over an area in a plane that is essentially orthogonal to an optical axis of the measuring system, said area including the optical axis of the measuring system or being spaced from said optical axis by no more than ⅙ of the diameter of the first convex lens,
- wherein the means is a flat mirror inclined relative to the optical axis.

12. The optical measuring system according to claim 1, wherein the lens array is coated with an anti-reflective coating on both sides.

13. The optical measuring system according to claim 1, wherein the measuring system is part of an intraoral dental camera.

14. The optical measuring system according to claim 13, wherein the intraoral dental camera has a handle, a front part that can be inserted into an oral cavity and a beam deflector arranged on a free end of the front part.

15. A method for optically measuring an object in a three-dimensional manner by means of an optical measuring system, comprising the steps of:
- illuminating beams reaching the object at least through a lens array and at least a first and a second convex lens in an order downstream of the lens array in a direction of propagation of the illuminating beams along an illuminating beam path, and
- absorbing a portion of the illuminating beams in an area upstream of or on the second convex lens in the direction of propagation of the illuminating beams or directed out of the illuminating beam path, said area including an optical axis of the optical measuring system or being spaced from said optical axis by no more than ⅙ of the diameter of the first convex lens,
- wherein the at least first and second lenses of the lens array are round and that the lens array has at least one space between the plurality of round lenses, and
- wherein the lens array is arranged in the optical measuring system in such a way that the optical axis of the measuring system passes through one of the spaces of the lens array.

* * * * *